US009486619B2

(12) United States Patent
Tyler et al.

(10) Patent No.: US 9,486,619 B2
(45) Date of Patent: Nov. 8, 2016

(54) INTERCONNECT DEVICES, SYSTEMS, AND METHODS FOR BRIDGING ELECTRONIC DEVICES

(71) Applicant: Case Western Reserve University, Cleveland, OH (US)

(72) Inventors: Dustin Tyler, Highland Heights, OH (US); Yueshuo Xu, Shaker Heights, OH (US); Allison Hess-Dunning, Cleveland Heights, OH (US); Christian Zorman, Euclid, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/619,560

(22) Filed: Feb. 11, 2015

(65) Prior Publication Data
US 2015/0229046 A1    Aug. 13, 2015

Related U.S. Application Data

(60) Provisional application No. 61/938,420, filed on Feb. 11, 2014.

(51) Int. Cl.
*A61B 5/04*   (2006.01)
*A61N 1/00*   (2006.01)
*A61N 1/05*   (2006.01)
*H01R 13/56*  (2006.01)
*A61N 1/36*   (2006.01)
*H05K 1/14*   (2006.01)

(52) U.S. Cl.
CPC .......... *A61N 1/0551* (2013.01); *H01R 13/562* (2013.01); *A61N 1/3605* (2013.01); *H01R 2201/12* (2013.01); *H05K 1/148* (2013.01)

(58) Field of Classification Search
USPC ........................................... 607/116; 600/372
See application file for complete search history.

(56) References Cited

U.S. PATENT DOCUMENTS

2011/0079423 A1* 4/2011 Zhao ...................... A61N 1/056
174/5 R

OTHER PUBLICATIONS

Aoki Mitsuhiro, et al. "Strain on the ulnar nerve at the elbow and wrist during throwing motion." J Bone Joint Surg Am 87.11 (2005): 2508-2514.

(Continued)

*Primary Examiner* — Nicole F Lavert
(74) *Attorney, Agent, or Firm* — Tarolli, Sundheim, Covell & Tummino LLP

(57) ABSTRACT

One aspect of the present disclosure can include an interconnect system for bridging electrical contacts. The system can include a first electrical contact, a second electrical contact, and an interconnect device that is coupled to and extends between the first and second electrical contacts. The interconnect device can include a flexible bridge and a non-linear conductive transmission line. The flexible bridge can have a length and an outer surface. The non-linear conductive transmission line can extend along, and encircle at least a portion of, the length of the bridge such that the non-linear conductive transmission line electrically connects the first electrical contact with the second electrical contact.

20 Claims, 12 Drawing Sheets

(56) References Cited

OTHER PUBLICATIONS

Hess-Dunning, Allison, Ph.D., et al. "Thin Film, High-Density Peripheral Nerve Cuffs" Advanced Platform Technology Center, pp. 1-5, VA (http://www.va.gov/) >> Health Care (http://www.va.gov/health) >> Advanced Platform Technology Center (/index.asp) >> Our Programs (/APTcenterresearch/programs/index.asp) >> Neural Interfaces (/APTcenterresearch/programs/neural/index.asp) >> Thin Film, High-Density Peripheral Nerve Cuffs.

Boretius, Tim, et al. "A transverse intrafascicular multichannel electrode (TIME) to interface with the peripheral nerve." Biosensors and Bioelectronics 26.1 (2010): 62-69.

Byl, Carolyn, et al. "Strain in the median and ulnar nerves during upper-extremity positioning." the Journal of hand surgery 27.6 (2002): 1032-1040.

Caldwell, C. W., and J. B. Reswick. "A percutaneous wire electrode for chronic research use." IEEE Transactions on Biomedical Engineering 5.BME-22 (1975): 429-432.

Demann, Eric TK, Pamela S. Stein, and James E. Haubenreich. "Gold as an implant in medicine and dentistry." Journal of long-term effects of medical implants 15.6 (2005).

Dilley, Andrew, et al. "Quantitative in vivo studies of median nerve sliding in response to wrist, elbow, shoulder and neck movements." Clinical biomechanics 18.10 (2003): 899-907.

Donaldson, P. EK. "The Craggs connector; a termination for Cooper cable." Medical and Biological Engineering and Computing 23.2 (1985): 195-196.

Fischer, Andreas C., et al. "Unconventional applications of wire bonding create opportunities for microsystem integration." Journal of Micromechanics and Microengineering 23.8 (2013): 083001.

Harman, George. Wire bonding in microelectronics, 3/E. McGraw Hill Professional, 2009.

Hess, Allison E., et al. "Development of a microfabricated flat interface nerve electrode based on liquid crystal polymer and polynorbornene multilayered structures." Neural Engineering, 2007. CNE'07. 3rd International IEEE/EMBS Conference on. IEEE, 2007.

Hess, "Design and Fabrication of Polynorbornene- and Liquid Crystal Polymer-Based Electrode Arrays for Biomedical Applications", Submitted in partial fulfillment of the requirements for the degree of Master of Science, May 2008, pp. 1-164.

Kratt, K. et al. "A fully MEMS-compatible process for 3D high aspect ratio micro coils obtained with an automatic wire bonder." Journal of Micromechanics and Microengineering 20.1 (2009): 015021.

Kratt, Kai, et al. "Solenoidal micro coils manufactured with a wire bonder." Micro Electro Mechanical Systems, 2008. Mems 2008. IEEE 21st International Conference on. IEEE, 2008.

K&S 4500 Series Manual Wire Bonders, Kulicke & Soffa Industries, Incorporated, Feb. 2002, pp. 1-251.

Lacour, Stéphanie P., et al. "Design and performance of thin metal film interconnects for skin-like electronic circuits." Electron Device Letters, IEEE 25.4 (2004): 179-181.

Lago, Natalia, et al. "Long term assessment of axonal regeneration through polyimide regenerative electrodes to interface the peripheral nerve." Biomaterials 26.14 (2005): 2021-2031.

Letechipia, Jorge E., et al. "In-line lead connector for use with implanted neuroprosthesis." IEEE transactions on bio-medical engineering 38.7 (1991): 707-709.

Leventhal, Daniel K., and Dominique M. Durand. "Subfascicle stimulation selectivity with the flat interface nerve electrode." Annals of biomedical engineering 31.6 (2003): 643-652.

Lewandowski, John J., et al. "Tension and fatigue behavior of 316LVM 1x 7 multi-strand cables used as implantable electrodes." Materials Science and Engineering: A 486.1 (2008): 447-454.

Lewandowski, John J., Ravikumar Varadarajan, and Brian Smith. "Tension and fatigue behavior of silver-cored composite multi-strand cables used as implantable cables and electrodes." Materials Science and Engineering: A 492.1 (2008): 191-198.

Lundborg, GÖRan, and BjÖRn Rydevik. "Effects of stretching the tibial nerve of the rabbit A preliminary study of the intraneural circulation and the barrier function of the perineurium." Journal of Bone & Joint Surgery, British vol. 55.2 (1973): 390-401.

Manson, S. S. "Fatigue: a complex subject—some simple approximations." Experimental mechanics 5.7 (1965): 193-226.

Meyer, Jörg-Uwe, et al. "High density interconnects and flexible hybrid assemblies for active biomedical implants." Advanced Packaging, IEEE Transactions on 24.3 (2001): 366-374.

Micera, Silvestro, et al. "On the use of longitudinal intrafascicular peripheral interfaces for the control of cybernetic hand prostheses in amputees." Neural Systems and Rehabilitation Engineering, IEEE Transactions on 16.5 (2008): 453-472.

Muralidharan, U., and S. S. Manson. "A modified universal slopes equation for estimation of fatigue characteristics of metals." Journal of Engineering Materials and Technology 110.1 (1988): 55-58.

Pecht, Michael, et al. Electronic packaging materials and their properties. CRC press, 1998.

Peckham, P. Hunter, and Jayme S. Knutson. "Functional Electrical Stimulation for Neuromuscular Applications*." Annu. Rev. Biomed. Eng. 7 (2005): 327-360.

Polasek, Katharine H., et al. "Human nerve stimulation thresholds and selectivity using a multi-contact nerve cuff electrode." Neural Systems and Rehabilitation Engineering, IEEE Transactions on 15.1 (2007): 76-82.

Prasad, Shankara K. Advanced wirebond interconnection technology. Springer Science & Business Media, 2004.

Rahimi, Rahim, et al. "A sewing-enabled stitch-and-transfer method for robust, ultra-stretchable, conductive interconnects." Journal of Micromechanics and Microengineering 24.9 (2014): 095018.

Rodriguez, Francisco J., et al. "Polyimide cuff electrodes for peripheral nerve stimulation." Journal of neuroscience methods 98.2 (2000): 105-118.

Scheiner, Avram, Gordie Polando, and E. Byron Marsolais. "Design and clinical application of a double helix electrode for functional electrical stimulation." Biomedical Engineering, IEEE Transactions on 41.5 (1994): 425-431.

Schiefer, Matthew A., et al. "Selective stimulation of the human femoral nerve with a flat interface nerve electrode." Journal of neural engineering 7.2 (2010): 026006.

Stieglitz, Thomas, M. Schuetter, and Klaus Peter Koch. "Implantable biomedical microsystems for neural prostheses." Engineering in Medicine and Biology Magazine, IEEE 24.5 (2005): 58-65.

Sunderland, Sydney, and K. C. Bradley. "Stress-strain phenomena in human peripheral nerve trunks." Brain 84.1 (1961): 102-119.

Tan, Daniel W., et al. "A neural interface provides long-term stable natural touch perception." Science translational medicine 6.257 (2014): 257ra138-257ra138.

Tyler, Dustin J., and Dominique M. Durand. "Chronic response of the rat sciatic nerve to the flat interface nerve electrode." Annals of biomedical engineering 31.6 (2003): 633-642.

Tyler, Dustin J., and Dominique M. Durand. "Functionally selective peripheral nerve stimulation with a flat interface nerve electrode." Neural Systems and Rehabilitation Engineering, IEEE Transactions on 10.4 (2002): 294-303.

Veraart, Claude, Warren M. Grill, and J. Thomas Mortimer. "Selective control of muscle activation with a multipolar nerve cuff electrode." Biomedical Engineering, IEEE Transactions on 40.7 (1993): 640-653.

Wright, Thomas W., et al. "Ulnar nerve excursion and strain at the elbow and wrist associated with upper extremity motion." The Journal of hand surgery 26.4 (2001): 655-662.

Ye, T., Z. Suo, and A. G. Evans. "Thin film cracking and the roles of substrate and interface." International Journal of Solids and Structures 29.21 (1992): 2639-2648.

* cited by examiner

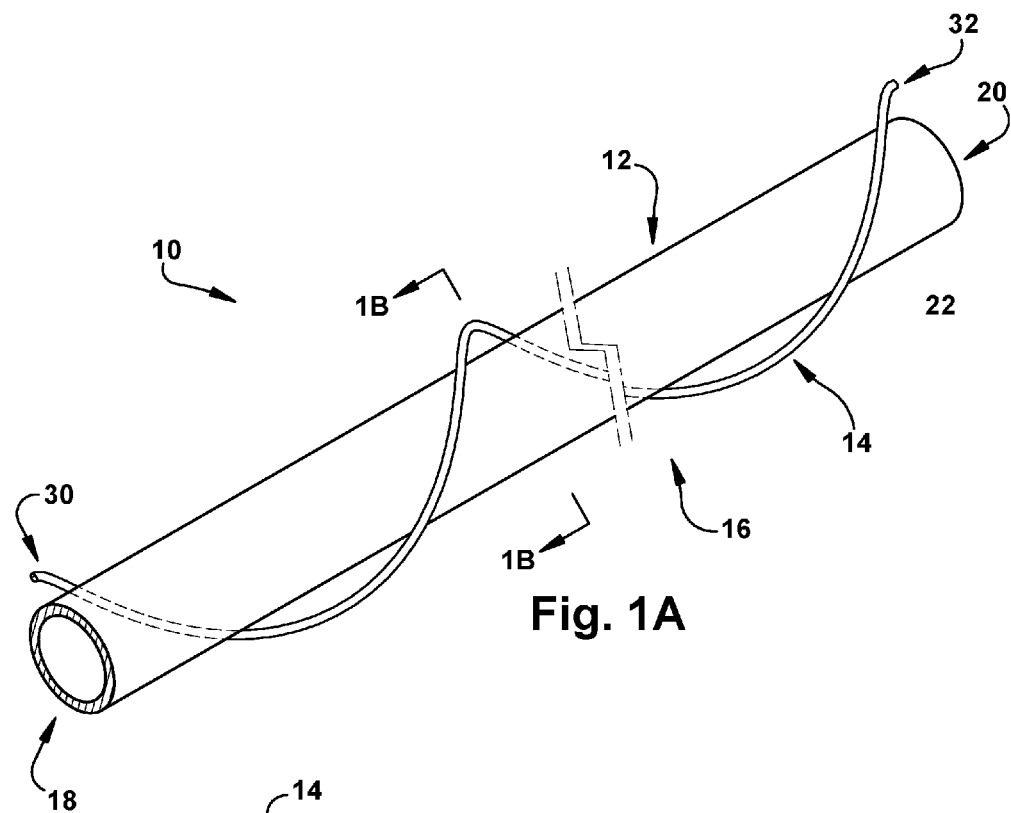
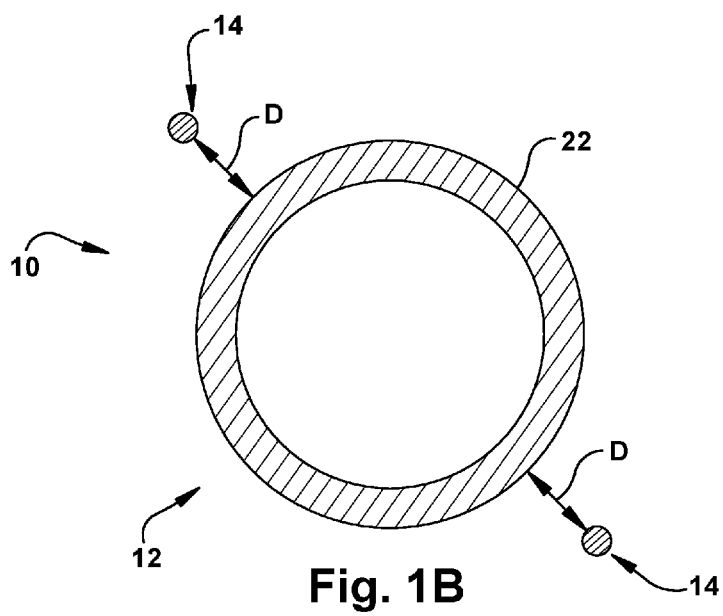

INTERCONNECT DEVICES, SYSTEMS, AND METHODS FOR BRIDGING ELECTRONIC DEVICES

RELATED APPLICATION

This application claims the benefit of U.S. Provisional Patent Application Ser. No. 61/938,420, filed Feb. 11, 2014, the entirety of which is hereby incorporated by reference for all purposes.

GOVERNMENT FUNDING

This invention was made with Government support under Grant No. RES 117485 awarded by the National Institutes of Health. The United States Government has certain rights in the invention.

TECHNICAL FIELD

The present disclosure relates generally to a flexible structure for interconnecting electronic devices and, more particularly, to devices, systems, and methods for maintaining electrical connection between electronic devices when the devices or systems are bent or otherwise deformed.

BACKGROUND

Functional electrical stimulation is the application of electrical current on excitable tissue to supplement or replace the function that is lost in neurologically impaired individuals. Electrical stimulation on neural tissue has been developed to restore function in upper extremity, lower extremity, bladder and bowel. This electrical activation of tissue can be realized via electrodes placed on nerves. Cuff-type electrodes are capable of selectively activating regions of a nerve trunk over an expanded range of opportunities for motor and sensory function restoration. Flat Interface Nerve Electrode (FINE) is one type of cuff electrode that is rectangular rather than cylindrical. The most recent version of FINE uses microfabricated thin film traces as an interconnect system between the electrode contacts and soldering pads connecting larger wires to external control devices. The thin film metal traces suffer from high resistance and can be damaged during repeated mechanical strains.

SUMMARY

One aspect of the present disclosure can include an interconnect device configured for interconnection between two electrical devices. The device can include a flexible bridge and a non-linear conductive transmission line. The flexible bridge can have a length and an outer surface. The non-linear conductive transmission line can extend along, and encircle at least a portion of, the length of the bridge.

Another aspect of the present disclosure can include an interconnect system for bridging electrical contacts. The system can comprise a first electrical contact, a second electrical contact, and an interconnect device that is coupled to and extends between the first and second electrical contacts. The interconnect device can comprise a flexible bridge and a non-linear conductive transmission line. The flexible bridge can have a length and an outer surface. The non-linear conductive transmission line can extend along, and encircle at least a portion of, the length of the bridge such that the non-linear conductive transmission line electrically connects the first electrical contact with the second electrical contact.

Yet another aspect of the present disclosure can include an implantable neurostimulator. The neurostimulator can comprise a first electrical contact, a second electrical contact, and an interconnect device that is coupled to and extends between the first and second electrical contacts. The interconnect device can comprise a flexible bridge and a non-linear conductive transmission line. The flexible bridge can have a length and an outer surface. The non-linear conductive transmission line can extend along, and encircle at least a portion of, the length of the bridge such that the non-linear conductive transmission line electrically connects the first electrical contact with the second electrical contact.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1A is a perspective view of a non-linear conductive transmission line encircling, but not directly contacting, a flexible bridge of an interconnect device for bridging electrical devices constructed in accordance with one aspect of the present disclosure;

FIG. 1B is a cross-sectional view taken along Line 1B-1B in FIG. 1A;

DETAILED DESCRIPTION

Definitions

Figure 2A:
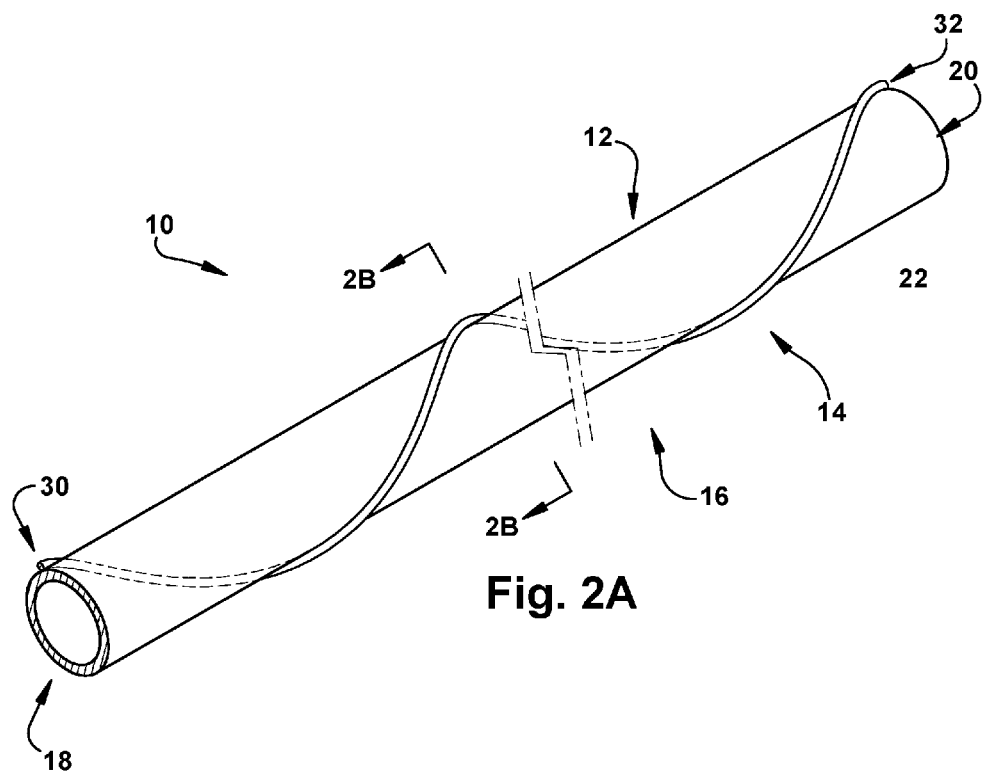
FIG. 2A is a perspective view showing an alternative construction of the interconnect device in FIGS. 1A-B.
Figure 2B:
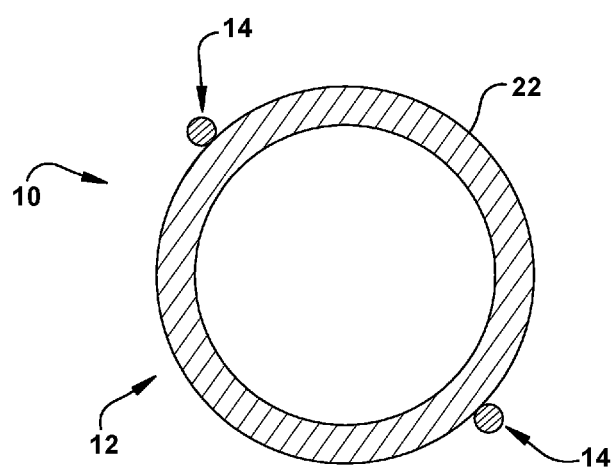
FIG. 2B is a cross-sectional view taken along Line 2B-2B in FIG. 2A.

Unless otherwise defined, all technical terms used herein have the same meaning as commonly understood by one of ordinary skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "electrical communication", "electrical connection", and "electrically connects" can be used interchangeably and refer to the ability of a generated electric field to be transferred to, or have an effect on, one or more components of the present disclosure. In some instances, the generated electric field can be directly transferred to a component (e.g., via a wire or lead). In other instances, the generated electric field can be wirelessly transferred to a component.

As used herein, the terms "flexible" or "flexibility" can refer to the ability of a material or body to deform elastically and return to its original shape when an applied stress is removed.

As used herein, the term "elastic" can refer to the behavior of a material or object, which, when subjected to an applied strain, at least a portion of the material or object extends in the direction of the strain, and when the applied strain is released, the material or object returns (to a degree) to its pre-strained condition.

As used herein, the term "electrical device" can refer to any electronic device, electronic module, electronic component, or even a mechanical device having an electrical component. An electronic device can include a finished product (e.g., an implantable medical device) or any type of structure that is incorporated into an electronic device and electronically connected to another structure in the device. Non-limiting examples of electrical devices can include medical devices (e.g., implantable medical devices, such as high-density electrode arrays, electrode leads, pacemakers and pacemaker components), consumer electronics, and other electronic components, such as MEMS devices, integrated circuits, printed wiring boards, integrated circuits, discrete components, connectors, flex circuits, displays, I/O interfaces, keypads and other input devices, and housings.

Overview

The present disclosure relates generally to a flexible structure for interconnecting electronic devices and, more particularly, to devices, systems, and methods for maintaining electrical connection between electronic devices when the devices or systems are bent or otherwise deformed. To electronically bridge electronic devices, discrete in-line connectors and high-density thin films are currently used. Such in-line connectors and thin film interconnects, however, suffer from high resistance and can be easily damaged during repeated mechanical strain. This is due, at least in part, to the fact that the conductive elements of such interconnect systems are often disposed on planar polymer substrates that allow for a small radius of curvature. A small radius of curvature is a more demanding configuration than a large radius of curvature. Consequently, the radius of curvature of a flexible polymer substrate can become so small that the ultimate strain of the conductive element(s) associated therewith is/are easily exceeded, thereby fracturing the conductive elements and resulting in a lost electrical connection between electronic devices.

Advantageously, the present disclosure overcomes the shortcomings of conventional interconnects by providing interconnect devices and systems that are sufficiently flexible so that upon bending or deformation, the devices and systems can bend or deform with the rest of the system and the electrical connection(s) between electrical devices is/are not broken or lost. As discussed in more detail below, the present disclosure is based, at least in part, on the development of an interconnect system comprising microwire helices disposed around a strain-relief material that can advantageously withstand short-term mechanical loads as well as 1.2 million cycles of 5% axial strain without significantly increasing resistance across a given electrical channel. Based on this, the present disclosure provides robust interconnect devices and systems that can reliably conduct electrical signals between electrical devices while also serving as a mechanical buffer therebetween. Thus, the present disclosure can find use in any electronic system (implantable or otherwise) that requires metallic interconnects.

Interconnect Devices

One aspect of the present disclosure can include an interconnect device 10 (FIGS. 1A-B) configured for interconnection between two electrical contacts. The interconnect device 10 can comprise a flexible bridge 12 and a non-linear conductive transmission line 14. As shown in FIGS. 1A-B, the flexible bridge 12 can include a main body portion 16 that extends between oppositely disposed first and second ends 18 and 20. The first and second ends 18 and 20 can be configured for connection to separate electrical devices. Thus, when the flexible bridge 12 is coupled between two electrical devices, the main body portion 16 is freely suspended therebetween, which, unlike planar in-line connectors and thin film interconnects, advantageously permits multiple degrees of freedom thereof. The flexible bridge 12 can have a length and an outer surface 22. The flexible bridge 12 can have any desired length, depending upon the particular application of the device 10. In one example, the length of the flexible bridge 12 can be about 2 cm.

The flexible bridge 12 can be made of any one or combination of materials, and have any desired configuration, so long as the flexible bridge is sufficiently flexible and elastic to allow it to deform when subject to mechanical strain (e.g., by bending, stretching, torque, crushing, etc.). In one example, the flexible bridge 12 can be configured as a silicone tube. In this instance, the flexible bridge 12 is hollow; however, it will be appreciated that all or only a portion of the flexible bridge may be solid. It will also be appreciated that the cross-sectional shape of the flexible bridge 12 can be circular (as shown in FIG. 1B), as well as any other suitable shape (e.g., rectangular, square, ovoid, etc.). The flexible bridge 12 can have any desired diameter (e.g., about 0.5 mm to about 1 mm or more). In one example, where the flexible bridge 12 has a tubular configuration, an outer diameter of the flexible bridge can be about 0.94 mm and an inner diameter of the flexible bridge can be about 0.51 mm.

The non-linear conductive transmission line 14 can comprise one or more electrically conductive elements. The non-linear conductive transmission line 14 can extend along, and encircle at least a portion of, the length of the flexible bridge 12. In some instances, the non-linear conductive transmission line 14 can comprise a single, discrete wire. All or only a portion of the wire can be insulated (e.g., with a dielectric material) or non-insulated. In one example, the non-linear conductive transmission line 14 can comprise a microwire having, for example, a diameter of between about 10 µm to about 75 µm (e.g., about 25 µm). The diameter (and thus cross-sectional area) of the non-linear conductive transmission line 14 can generally be greater than the cross-sectional area of thin film metal traces and, thus, the unit length resistance for the non-linear conductive transmission line is significantly smaller compared to the unit length resistance for the thin film traces. Advantageously, the channel resistance associated with the non-linear conductive transmission line 14 is substantially less than the resistance associated with thin film metal traces. In other instances, the non-linear conductive transmission line 14 can comprise a ribbon cable (e.g., an insulated, multi-channel polyimide ribbon cable). The non-linear conductive transmission line 14 can be made of one or a combination of electrically conductive materials, such as aluminum, copper or gold.

The non-linear conductive transmission line 14 can have a helical or spiral-shaped configuration. The helical or spiral-shaped configuration advantageously provides the non-linear conductive transmission line 14 with flexibility in three dimensions, which is in contrast to thin-film structures that are largely confined to two-dimensional structures. As shown in FIGS. 1A-B, the non-linear conductive transmission line 14 can be radially spaced apart from the outer surface 22 of the flexible bridge 12 at a distance D such that the non-linear conductive transmission line is free from direct contact therewith (e.g., either with or without the device being subject to a mechanical strain). In this configuration, the distance D can decrease when the device 10 is subject to mechanical strain. This advantageously allows the non-linear conductive transmission line 14 to deform about the flexible bridge 12 but without overly constricting the flexible bridge so as to cause breakage. In an alternative configuration, all or only a portion of the non-linear conductive transmission line 14 can be in direct contact with the outer surface 22 of the flexible bridge 12 (e.g., either with or without the device being subject to a mechanical strain).

The non-linear conductive transmission line 14 can be configured about the flexible bridge 12 as either a right-handed helix or a left-handed helix. A right-handed helix, for example, can refer to a helix that moves away from a starting point in a clock-wise helical motion. Any number of revolutions of helices can extend along the flexible bridge 12. In one example, 10-12 helices can extend along the flexible bridge 12. The pitch angle of the non-linear conductive transmission line 14 can be varied as needed depending upon the construction of the device 10 and its intended application. Since the pitch angle will decrease as the non-linear conductive transmission line 14 is stretched in the axial direction, the pitch angle can be sufficiently large to permit axial stretching but without excessive constriction of the non-linear conductive transmission line about the flexible bridge 12.

Generally speaking, the number of contact channels on a given electrical device will determine the number of non-linear conductive transmission lines 14 comprising the interconnect device 10. Thus, in another aspect, the device 10 can include two or more non-linear conductive transmission lines 14. In some instances, two or more non-linear conductive transmission lines 14 can be configured to extend in parallel to one another about the flexible bridge 12. In other instances, two or more non-linear conductive transmission lines 14 can be configured to extend in an opposite direction as one another, essentially like a DNA helix. Advantageously, the non-linear conductive transmission line 14 along with the flexible bridge 12 of the device 10 provides a strain-relief mechanism that, even when subject to short and long-term mechanical deformation, maintains an electrical connection between two electrical devices.

Interconnect Systems

Another aspect of the present disclosure can include an interconnect system 24 (FIGS. 3-4) for bridging electrical contacts. The system 24 can comprise a first electrical contact 26, a second electrical contact 28, and an interconnect device 10 that is coupled to, and extends between, the first and second electrical contacts. The interconnect device 10 can be configured as described above and include, for example, a flexible bridge 12 and a non-linear conductive transmission line 14 that extends along, and encircles at least a portion of, the outer surface 22 of the flexible bride. The non-linear conductive transmission line 14 can be further configured such that it includes first and second ends 30 and 32 configured for electrical connection to the first and second electrical contacts 26 and 28, respectively, so that the first and second electrical contacts are in electrical communication with one another.

Figure 3:
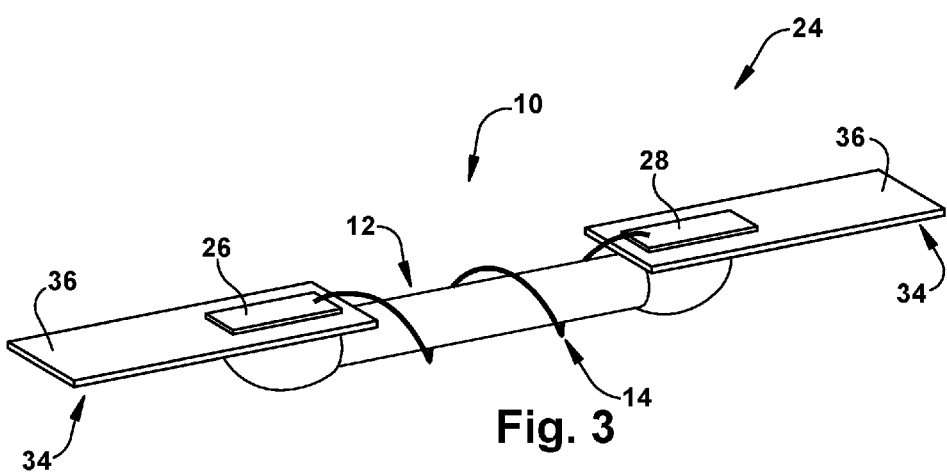
FIG. 3 is a perspective view of an interconnect system for bridging electrical devices constructed in accordance with another aspect of the present disclosure.

The first and second electrical contacts 26 and 28 can include any electrically conductive structure, element, or component comprising an electrical device. In some instances, each of the first and second electrical contacts 26 and 28 can be disposed on separate dielectric substrates 34, each of which has a first surface 36 and a second surface 38. As shown in FIG. 3, the first and second electrical contacts 26 and 28 can be disposed on the first surface 36 of each of the dielectric substrates 34. The respective ends 30 and 32 of the non-linear conductive transmission line 14 can be electrically connected to the first and second electrical contacts 26 and 28. Suitable methods for connecting the non-linear conductive transmission line 14 between the first and second electrical contacts 26 and 28 can include wire bonding, ball bonding, soldering and/or application of an adhesive (e.g., epoxy). Examples of electrical devices that can be bridged by the system 24 are discussed herein. However, it will be appreciated that the system 24 can find use in a variety of other implantable and non-implantable electronic systems, such as biomimetic body implants and human-machine interfaces.

Figure 4:
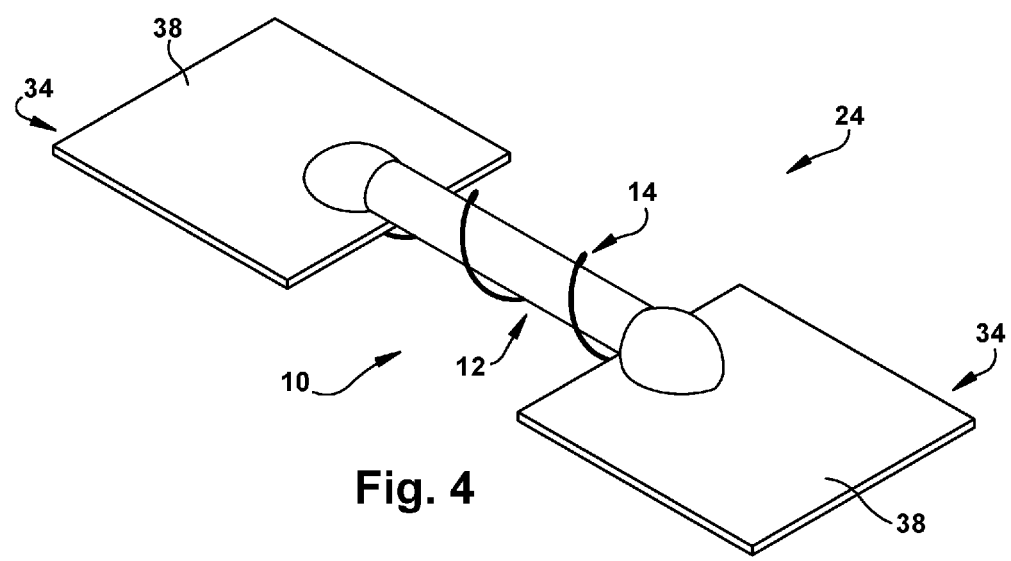
FIG. 4 is a different perspective view of the interconnect system in FIG. 3.

Referring to FIG. 4, the first and second ends 18 and 20 of the flexible bridge 12 can be physically coupled or connected to different dielectric substrates 34 comprising separate electrical devices. In one example, the first and second ends 18 and 20 of the flexible bridge 12 can be connected to the different dielectric substrates 34 using an adhesive (e.g., a silicone epoxy).

Methods

Another aspect of the present disclosure can include a process for constructing an interconnect device 10 and system 24. A coil-winding machine is often used to coil microwires along mandrels. Conventional micro-winding machines are used to fabricate microcoils that are part of intravascular catheter and electrodes. They are easy to operate in terms of controlling the winding parameters, but they are not designed to work with bonding wires. In addition, they often require a cylindrical mandrel for the wire to coil around. Existing micro-winders are too bulky to be held as a mandrel on a conventional coil-winding machine.

Figure 5:
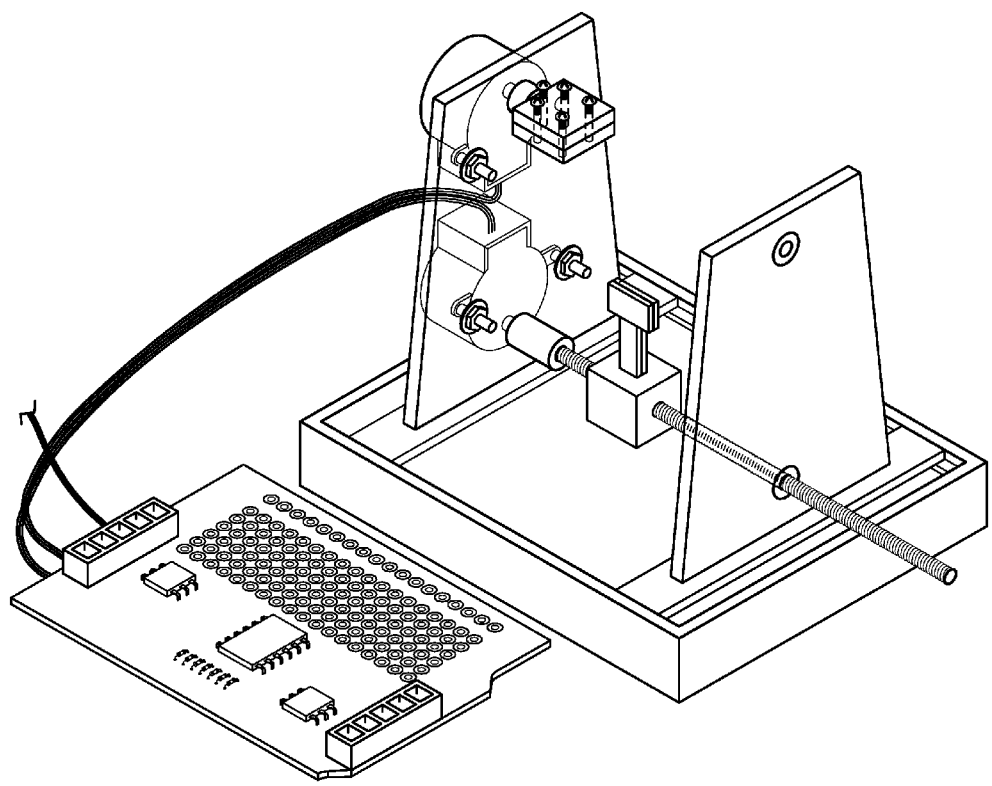
FIG. 5 is an image of a microwinder used to construct one example of an interconnect system for bridging electrical devices according to another aspect of the present disclosure.

Advantageously, a method for constructing an interconnect system 24 according to the present disclosure can use a microwinder assembly as illustrated in FIG. 5. The microwinder assembly can include a microprocessor, two stepper motors, a threaded rod to change rotational motion into translational motion, and laser cut acrylic constructed base, clip holding stages, wire clamp, and a clamp moving shuttle. The microprocessor can control two servomotors that rotate at different angular velocities. The stage rotating motor can control the rotation of the stage holding a supporting structure (e.g., flexible bridge 12), while the wire clamp moving motor can rotate the threaded rod to move the wire clamp with the shuttle from left to right. The angular velocity ratio of the two motors can determine the helix pitch angle, which is programmable based on the desired pitch angle. The components of the microwinder can be optimized depending upon the type of electronic devices sought to be bridged by the interconnect system 24. One example of a microwinder, and its operation in constructing an interconnect system 24 for a high-density electrode array, is described in the Example below.

One challenge associated with thinner or longer non-linear conductive transmission lines 14 (e.g., microwires) is preventing wire sweep and shorts, which can occur during molding of wire bond packages. Advantageously, the wire clamp of the microwinder (FIG. 5) is configured to hold multiple microwires in parallel and move along the flexible bridge 12 (e.g., silicone tube) while the bridge and electrical contacts rotate. Coiling the microwires together can thereby reduce the chance of shorting as compared to coiling one microwire at a time. Moreover, unlike conventional microwinders, the microwinder of the present disclosure is advantageously configured to: hold the supporting structure (e.g., flexible bridge 12) while coiling the non-linear conductive transmission line 14 (e.g., helical microwire) in a slow and controlled fashion; coil multiple non-linear conductive transmission line for different channels simultaneously to guarantee that the lines stay separated; and assist the winding process to control the pitch angle of the helix and parallel line separation.

Another aspect of the present disclosure can include application of the interconnect device 10 and system 24 in a variety of environments for both short-term and long-term use. In some instances, the interconnect device 10 and/or system 24 can find application in consumer electronics where, for example, the interconnect system and/or device may be used to bridge two electrical devices, such as MEMS devices, integrated circuits, printed wiring boards, integrated circuits, discrete components, connectors, flex circuits, displays, I/O interfaces, keypads and other input devices, and housings.

In other instances, the interconnect system 24 and/or device 10 can be used to bridge implantable medical devices and/or electronic components thereof. In one example, the interconnect system 24 and/or device 10 can find use in the functional electrical stimulation (FES) field, which generally includes devices and methods for applying electrical current to excitable tissue(s) to supplement or replace the function(s) that is/are lost in neurologically-impaired subjects. Cuff-type electrodes are commonly used for FES. One type of cuff electrode, the Flat Interface Nerve Electrode (FINE), uses microfabricated thin film traces as an interconnect system between the electrode contacts and soldering pads connecting larger wires to external control devices. The metal traces on a flexible substrate comprising cuff-type electrodes (such as the FINE), however, can be subjected to a much higher localized strain that is beyond the ultimate strain limit of the metal trace when the substrate is bent or stretched. Exceeding the ultimate strain limit results in cracking of the thin film, which negatively affects the conductivity of the channels.

Advantageously, the interconnect device 10 and/or system 24 can be used as an alternative to the thin film metal traces comprising conventional neurostimulation devices, such as multi-channel cuff-type electrodes. An implantable neurostimulator comprising the interconnect device 10 and/or system 24 can maintain electrical conductivity between electrical contacts under both short-term and long-term mechanical load. Short-term mechanical load can result from stretching, bending, twisting, and other deformation associated with fitting the implantable neurostimulator on a target nervous tissue (e.g., a nerve) during the surgical implantation procedure. In addition, an implantable neurostimulator comprising the interconnect device 10 and/or system 24 can maintain electrical conductivity between electrical contacts under static and cyclic load for many years post-implantation. Since, in some instances, the neurostimulator will track the target nervous tissue (e.g., nerve) in terms of elongation under the most severe conditions, the interconnect device 10 and/or system 24 comprising the neurostimulator can advantageously also experience a less or equal amount of strain as the nerve but without a loss of electrical conductivity between electrical contacts.

The following example is for the purpose of illustration only and is not intended to limit the scope of the claims, which are appended hereto.

Example

The following Example illustrates an interconnect system, constructed in accordance with one aspect of the present disclosure, demonstrating the ability to survive short-term 20% axial strain, one revolution clockwise and counter-clockwise torsional strain, 180° bend along its bridge, and long-term 5% cyclic axial strain for 1.2 million cycles.

Methods

A. Interconnect Device Design and Fabrication

1. Design

The design of the microwire helix was considered as an alternative to thin-film metal trace interconnects. A small silicone tube provided both structural support and stress relief for the helical wires. Biomedical silicone tubing (806400, A-M Systems, Sequim, Wash.) with 0.037 in (0.94 mm) outer diameter and 0.02 in (0.51 mm) inner diameter was selected to be close to the width of the thin film interconnect segment. A 2 cm long tube was connected to two 5 mm by 5 mm silicon dioxide ($SiO_2$) bond chips with small amount of Silicone adhesive. The bond chips were coated with 20 nm of Titanium (Ti) adhesion layer between the substrate and a 250 nm Gold (Au) layer on top. The metal films were photolithographically patterned and etched using Au etchant and buffered oxide etchant to leave Au/Ti bonding pad arrays. The bond pads have widths ranging from 250 μm to 1 mm with both circular and square shapes.

2. Microwinder Operation

A coil-winding machine is often used to coil micro-wires along the mandrels. Currently available micro-winding machines are used to fabricate micro-coils that are part of the intravascular catheter and electrodes. They are easy to operate in terms of controlling the winding parameters, but they are not designed to work with bonding wires. In addition, they often require a cylindrical mandrel for the wire to coil around. The supporting structure of the microwire helix interconnect design is bulky to be held as a mandrel on a conventional coil-winding machine. An apparatus needed to be designed to hold the supporting structure while coiling the small wires in a slow and controlled fashion. However, since the wires used in the device fabrication were not insulated, the apparatus needed to be able to coil multiple wires for different channels simultaneously to guarantee that the wires stay separated.

A micro-winder that fits the design requirements was developed to assist the winding process to control the pitch angle of the helix and parallel wire separation (FIG. 5). The entire assembly includes a microprocessor, two stepper motors, a threaded rod to change rotational motion into translational motion, and laser cut acrylic constructed base, clip holding stages, wire clamp, and clamp moving shuttle. The microprocessor controls two servomotors that rotate at different angular velocities. The stage rotating motor controls the rotation of the stage holding the supporting structure, while the wire clamp moving motor rotates the threaded rod to move the wire clamp with the shuttle from left to right.

The angular velocity ratio of the two motors determines the helix pitch angle, which is programmable based on the desired pitch angle. Since this device was designed, in one application, for high-density electrode array (e.g., FINE with 32 leads), the goal was to construct more than one wire helix in parallel along the tube to provide connections for individual contact. The pitch angle calculation and corresponding angular velocity ratio calculation is presented below.

$$\text{angular velocity of the stage: rode linear velocity} = \frac{D_{tube}\pi/t}{2L_o/t} \quad \text{Equation 1}$$

Where $D_{tube}$ is 0.94 mm representing the diameter of the tube, $L_0$ is 0.8 mm representing the initial separation between each wrap of the same wire in the most compacted condition, t is the time required to move the wire clamp 0.8 mm horizontally while the stage completes one circle of rotation. The separation between each wrap for the same wire was assumed to be 0.8 mm with 32-25 μm diameter wires tightly aligned with negligible separation distance. This micro-winder system wrapped two wires each time to simulate the pitch angle of 32 tightly aligned wires. The calculated ratio between the stage angular velocity to the linear velocity of the rod was 1.85. The translational velocity and angular velocity of the threaded rod depended upon the thread pitch distance and the rod major diameter.

$$\text{Rod linear velocity: angular velocity} = \frac{\text{thread pitch distance}}{\text{major } D \text{ circumference}} \quad \text{Equation 2}$$

Where the thread pitch distance is 0.7938 mm, and the major diameter circumference is 4.826 mm. The ratio between the linear velocity and the angular velocity of the rod is 0.1645. By multiplying Equations 1 and 2, the stage angular velocity to rod angular velocity ratio is obtained as Equation 3:

angular velocity of the stage: angular velocity of the rod=1.85×0.1645=0.3

3. Supporting Structure Assembly

The supporting structure (or bridge) included a piece of 2 cm long silicone tubing and 2 bond chips that were adhered to either end of the tubing with silicone adhesive. The length of the silicone tubing was determined based on the length of the thin film trace interconnect. A piece of wire threaded through the lumen of the silicone tube was used to provide some rigidity to the flexible structure during the fabrication process. The supporting wire was later removed after completing the assembly process.

4. Helix Formation

The next step was to temporarily adhere two 25 μm diameter Au bonding wires with silicone adhesive to one chip so that the wires would be stationary during the bonding process. This assembly was later fixed onto the wire bonder (4700 Manual ball bonder, Kulicke & Soffa, Singapore). Wire bonds connect the wire and bonding pads both mechanically and electrically. Three sets of ball-stitch bonds were stacked on and next to each wire. The thermosonic ball-stitch bonding mechanism was used in this study because the ball bond has 360° of freedom, allowing the stitch bond to be placed optimally to capture and secure the end of the wire helix.

The wire clamp, made out of two pieces of acrylic with a layer of silicone sheet on each piece, held the free ends of the bonding wires with previously cut slots on silicone sheet. Then, the two pieces of acrylic were fixed together with a screw to enclose the ends of the bonding wires in the gap between the two sheets of silicone.

The skeleton structure was mounted on the upper rotating stage with the wire-bonded chip clamped on the stage. The free ends of the two wires were fixed by the wire clamp on the bottom. The wires secured by the wire clamp were pulled straight after the clamp was mounted on the shuttle. A screw tightened the wire clamp to control the tension on the winding wires, and hence the force applied to ensure that the wire is deformed during the winding process. When both motors started to rotate with programmed velocity, wires coiled along the tube. As wires started wrapping on the tube, more length was pulled through of the wire clamp. The helices are right-handed, meaning that the helices moved away from the starting point in a clock-wise helical motion. Generally, 10 to 12 revolutions of helices were formed between the two substrates. Then the free ends of the wires were temporarily attached onto the unbonded chip and bonded with the same process as bonding the wires on the first substrate. The wire bonds were secured with epoxy (H54, Epoxy Technology, Billerica, Mass.) to increase the robustness of the system and eliminate any failure at the wire bonds. The epoxy was mixed with 10:1 base to curing agent ratio and dispensed with a micro dispenser. Larger wires (32 gauge wire with enamel coating) were attached with conductive epoxy (CircuitWorks conductive epoxy, Chemtronics, Kennesaw, Ga.) to the microwires for electrical measurement purposes.

B. Tensile Test

A tabletop tensile tester (Model 1130, Instron Corporation, Norwood, Mass.) was used to measure the ultimate elongation of the test structures. Two bond chips on either side of the interconnect system were anchored on the two Instron clamps to orient the sample perpendicular to the horizontal surface. The clamp on the bottom was stationary while the clamp on the top was attached to the crosshead that can be driven up or down with electromechanical force. All samples were tested to failure with a crosshead displacement rate of 5 mm/min along with a 5-lbs load cell and MTS Testworks software (MTS Systems, Eden Prairie, Minn.). Both load and displacement were recorded with the MTS Testworks software with a data acquisition rate of 10 Hz. Engineering strain was calculated using the crosshead displacement divided by the gauge length, which is the approximate length of the tubing with adhesive on both ends (i.e., (displacement/gauge length)×100). In this test, the Instron is sensitive enough to detect the breaking of the wires and indicate the points of breaking as local maxima on the stress strain plots. From several trial studies connecting the channels to a wire breaking detection system, the local maxima shown on the stress strain recorded data matched with the detection system indicated wire breaking. Ultimate tensile strain for each sample was recorded on the stress strain curve as the first local maximum when the first wire broke.

C. Torsion Test

The interconnect device may experience torsion forces along the axis of the helices during the implantation procedure. Initially, two samples were tested for their ultimate failure point under clockwise rotation and one sample under counterclockwise rotation. 5 samples were tested for the design criteria of 180° clockwise to 180° counterclockwise rotation. Since none of these 5 samples failed, all 5 samples passed the design criteria. From this batch, 2 samples were tested to clockwise rotation failure in additional to the 2 samples tested earlier.

Figure 6:
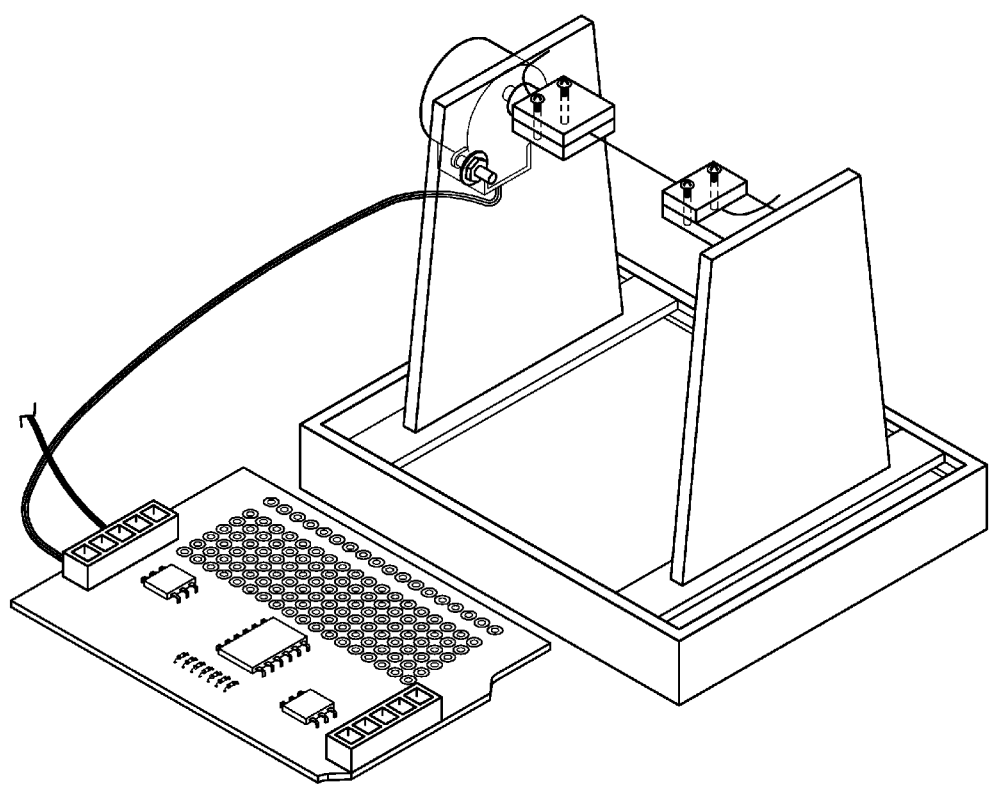
FIG. 6 is an image of a torsion test apparatus according to another aspect of the present disclosure.

A torsion test apparatus was modified based on the micro-winder developed for this test (FIG. 6). A servomotor rotated the stage attached to the motor while the other stage stayed fixed. The two silicon chips on either side of the tube were clamped separately on the two stages and the tube was aligned with the axis of rotation of the servomotor. The four measuring wires were connected to the wire breaking detection system. A computer connected to the microprocessor that powers the servomotor recorded the number of steps the servomotor rotated. When the wire breaking detection system indicated wire breaking, the microprocessor was manually disconnected from the computer to stop the servomotor motion. The degree of rotation could then be calculated knowing the current number of steps and that the servomotor rotated 513 steps for a complete revolution. Therefore, the degree of rotation can be calculated as (current step/513)× 360°.

D. Bend Test

The interconnect device may bend around the axis that is perpendicular to the tube during the surgical operation. 3 samples were bent 360° with different bending radii. The diameters of 5 solid cylinders selected for this test are listed in Table 1.

TABLE 1

| Selected 5 radii for bending test | | | | |
|---|---|---|---|---|
| D1 | D2 | D3 | D4 | D5 |
| Bending Radius 1.22 mm | 1.47 mm | 1.96 mm | 2.49 mm | 3.10 mm |

D5 is the least bent condition for the sample to complete a 360° wrap without stretching the tube and helices. In the bending test, the interconnect device was bent 360° around D5. Then the same device was bent around D4 to D1 with the same process and around D1 for 20 times at the end. Resistance measurements were collected in these six configurations: straight sample, microwire helix curled around D5 to D1. Finally, the resistance values were recorded after the microwire helix curled around D1 for 20 times. This procedure was repeated on three independent samples.

Figure 7:
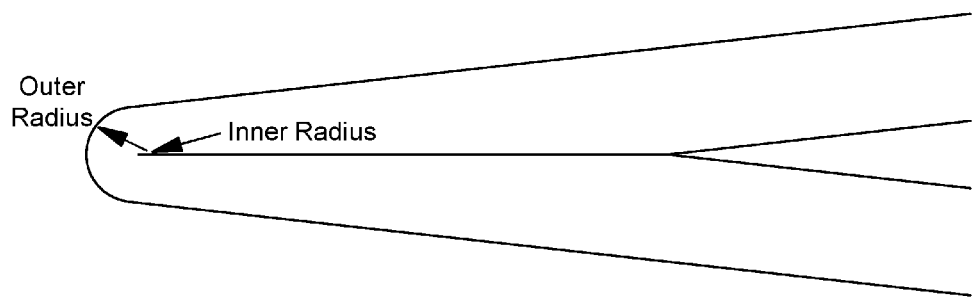
FIG. 7 is a schematic illustration showing an extreme bending condition with zero inner bending radius.

We defined the extreme bending condition as the bending radius at which the tube collapses when flexed 180°. This condition is shown in FIG. 7. The outer radius was measured three times to calculate the strain along a piece of bonding wire that was placed along the tube and bent 180° with the tube.

$$\varepsilon = \frac{2\sigma}{E} = \frac{d}{\rho} \qquad \text{Equation 4}$$

where $\varepsilon$ is the strain along the bonding wire, d is the diameter of the bonding wire, and $\rho$ is the outer radius defined by the extreme bending condition of the bent tube. The strain experienced by the wire during bending is less when the wire is in the helix configuration compared to when wire is aligned in parallel with the tube. If the bending strain does not exceed the wire ultimate tensile strain under the extreme bending condition when the wire is aligned in parallel with the tube, the bonding wires in the helix configuration will not break under the same level of bending strain.

E. Fatigue Test

Since this device will be considered for chronic implantation, the fatigue response of the device was analyzed for the life span of 10 years under different strains. All fatigue tests were completed on Enduratec (S-A02601C, Bose, Eden Prairie, Minn.) with 5 lbs load cell and WinTest Controls (Series 4.1, Bose, Eden Prairie, Minn.). The two bond chips on the sample were clamped on the machine and stretched longitudinally with a one amplitude sinusoidal waveform with 0 being the minimum and the selected amplitude being the maximum. During the fatigue test, the electrical continuity of the wires was measured by a wire breaking detection system. Fred Montague from Functional Electrical Stimulation center developed this system for testing the life cycles of the multi-strand implantable cable on Enduratec. This system contains 9 individual channels that can measure the continuity between two leads. It takes in 5-10 V input voltage to power D flip-flops for continuity detection. While the wires on the interconnect device stay conductive, the break detection system will output the same amount of voltage as the input. When one wire breaks, the output will be switched to zero and the LED light of the corresponding channel will be turned on indicating wire breaking. Enduratec will be stopped once the output measurement drops below the stopping threshold preset on WinTest, and the number of cycles reached before interconnect device failure will be recorded.

People with different daily activities use their limbs differently, and therefore subject the interconnect device to a different number of cycles over the 10-year lifetime. Based on the past fatigue tests done on the multi-stranded implantable cables for upper limb and communication with the research team, we assume upper limb nerves stretch 20 times per hour during 16.5 hours of activity per day on average. The device, which is implanted along the nerves, need to survive 1.2 million cycles for 10 years lifetime. The test frequency was 3 Hz based on the normal functioning frequency of the fatigue test machine. The test was 540 times faster than real-life situation by taking the ratio between 3×3600 (number of cycles per hour during the test) and 20 (number of cycles per hour in reality). 4-5 days is the estimated required time to complete 1.2 million cycles. Strain levels ranging from 5% to 25% representing normal physiological elongation and extreme conditions, were tested. Cadaver studies reported that typical maximum nerve strain in the upper limbs is 15% with occasional single measurement approaching 20%. Therefore, the interconnect device is expected to survive 1.2 million cycles under 5% cyclic displacements. To investigate the device long-term behavior, 5%, 10%, 15%, 20%, and 25% strains were also tested to generate a fatigue curve for future predictions of device lifetime under certain cyclical displacement.

Results

A. Resistance Measurement

The resistance across each bonding wire helix can be predicted based on the resistivity of Au bonding wires, wire cross sectional area, and wire segment length. The resistivity of 25 μm diameter Au bonding wire is $2.2 \times 10^{-6}$ Ω-cm. The resistance per unit length based on this standard resistivity value is, $$\frac{R}{L} = \frac{\rho}{A} = 0.45 \ \Omega/cm \quad \text{Equation 5}$$

The average resistance measured from the all the channels in 14 samples is 3.31±0.28Ω. Knowing that the actual separation between each wrap is approximately 1 mm and the number of revolution is 10-12, the length of the wire can be predicted as:

$$L = 10 \times \sqrt{\pi D_{tube}^2 + 1mm^2} = 3.12 \ cm \quad \text{Equation 6}$$

The calculated resistance per unit length based on experimental resistance measurements is 1.06±0.09 Ω/cm. The discrepancy from the measured predicted resistance is due to the resistance additive effect of the measuring wire, conductive epoxy and wire bonds.

B. Ultimate Tensile Test

Figure 8:
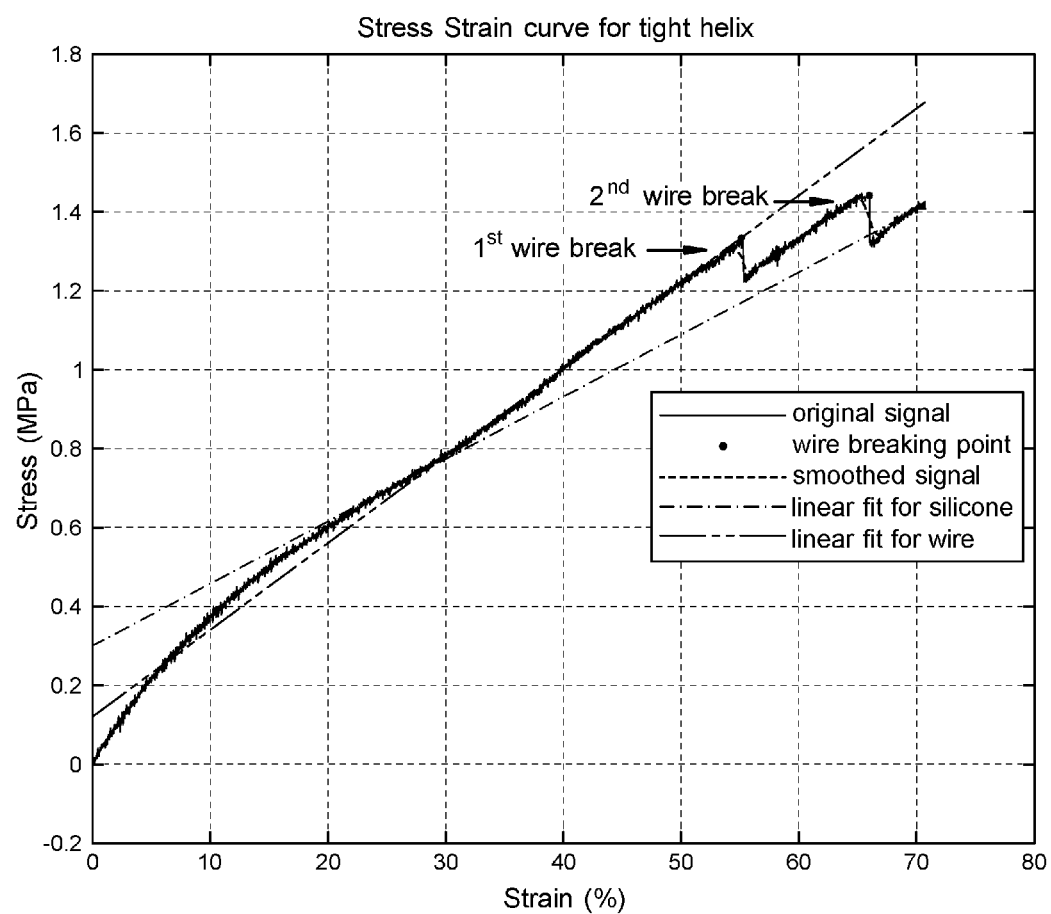
FIG. 8 is a stress-strain curve of an uncoated interconnect system with two parallel bonding wires.

When the entire device elongated, the cross sectional area of the helix decreased with the cross sectional area of the silicone tube. Until the diameter of the helix became smaller than the diameter of the stretched tube, the helix tightened on the tube and broke at the junction where wires cross from the bond chips to the tube. The ultimate tensile strain information was collected from the Instron stress-strain curve shown in FIG. 8. The true strain in FIG. 8 was calculated by dividing the crosshead displacement by the original separation between the Instron clamps, which is the length of the stretched region including the tubing and silicone adhesive on both ends of the tubing. The first local maximum point in FIG. 8 indicates when the first bonding wire broke. The corresponding strain of the first local maximum was recorded as the ultimate tensile strain of the coiled system. The estimated ultimate strength at the first local maximum is the ratio between the applied force and the original cross sectional area of the tubing. From 10 independent samples, their ultimate tensile strain and strength by taking the ratio of load and tube cross sectional area are included in Table 2.

TABLE 2

Ultimate failure strength, strain and modulus for 10 independent samples

| Sample | Ultimate Strain (%) | Ultimate Strength (MPa) |
|---|---|---|
| 1 | 55.33 | 1.336 |
| 2 | 87.50 | 1.847 |
| 3 | 34.70 | 1.063 |
| 4 | 57.86 | 1.316 |
| 5 | 65.12 | 1.510 |
| 6 | 54.74 | 1.490 |
| 7 | 44.91 | 1.146 |
| 8 | 51.86 | 1.173 |
| 9 | 63.05 | 1.227 |
| 10 | 67.03 | 1.663 |
| Mean | 58.21 | 1.377 |
| Standard Deviation | 14.13 | 0.248 |

The pitch angle of the helix is constant. The number of revolutions was controlled between 10 and 12 depending on the length of the tubing between the bond chips. The ultimate strain values of the samples varied based on the fabrication process of the samples. The average ultimate strain is 58.21±14.13%. The confidence interval for the ultimate failure point is (44.91, 67.03) with 97.85% of confidence (1-sample Sign Test). The ultimate strain of the microwire helical structures were significantly larger than 4%, which is the ultimate strain of the standard straight Au bonding wires (p=0.003, 1-sample Wilcoxon Test) supporting the hypothesis that the microwire helix interconnect system can sustain a larger percent of displacement in comparison to straight bonding wires. The ultimate strain of the interconnect system is also significantly larger than the 18% peripheral nerve stretching limit when microcirculation is stopped (p=0.003, 1-sample Wilcoxon Test).

C. Ultimate Torsion Test

The five samples that were twisted 180° clockwise to positive 180° and then 360° counterclockwise to negative 180° all passed this validation test. Two of them were twisted until the wires broke. The ultimate failure points of four samples for clockwise rotation are presented in Table 3.

TABLE 3

Torsion test ultimate failure points for four independent samples

| Sample # | Number of revolutions |
|---|---|
| 1 | 16.4 |
| 2 | 13.4 |
| 3 | 15.9 |
| 4 | 13.5 |

The number of revolutions was calculated based on the microprocessor measurement of total number of steps step motor moved divided by the number of steps in each revolution. Based on the result in Table 3, according to nonparametric 1-sample sign test, there is 87.5% of chance that the failure point of the interconnect device is in the range of 13.4 to 16.4 revolutions. This is beyond the torsional displacement expected in service.

Since all the helices are right-handed, the breakage of the wires only occurred when rotating the substrate counterclockwise relative to the stationary substrate. The silicone tube initially twisted with the bonding wires. The helices were stretched and constricted on the tube when the tube was twisted. When the tension on the wires exceeded the ultimate strength, the wire broke in the middle of the helix. When rotating the substrate clockwise relative to the stationary substrate, the helix unwound itself after 3.57 revolutions. This kind of rotation was only tested on one sample. Rotating back counterclockwise after the helix unwound did not restore the helix back to its original structure.

D. Short-Term Bend Test

Three samples were bent 360° around 5 different bending radii. The resistance values across both channels were measured when bent to compare to the original resistances (Table 4).

TABLE 4

Bend test resistance measurement

| | Sample 1 | | Sample 2 | | Sample 3 | |
|---|---|---|---|---|---|---|
| | R1 (Ω) | R2 (Ω) | R1 (Ω) | R2 (Ω) | R1 (Ω) | R2 (Ω) |
| Original | 3.3 | 3.4 | 3.8 | 3.6 | 3.1 | 3.2 |
| Around D5 | 3.3 | 3.4 | 3.8 | 3.5 | 3.4 | 3.3 |
| Around D4 | 3.4 | 3.3 | 3.5 | 3.9 | 3.1 | 3.2 |
| Around D3 | 3.4 | 3.4 | 3.8 | 3.6 | 3.3 | 3.2 |
| Around D2 | 3.4 | 3.4 | 3.9 | 3.6 | 3.4 | 3.3 |
| Around D1 | 3.4 | 3.4 | 3.9 | 3.6 | 3.1 | 3.2 |
| 20 bends D1 | 3.4 | 3.4 | 3.8 | 3.4 | 3.2 | 3.3 |

The resistance across the bonding wire would increase to infinite if the wire breaks. According to the measurement, the maximum resistance change on sample 1 was approximately 3% when resistance changed from 3.3Ω to 3.4Ω. On sample 2, the resistance changed about 11.4% when resistance increased from 3.5Ω to 3.9Ω. On sample 3, when resistance of channel 1 increased from 3.1Ω to 3.4Ω, there was 9.7% change in resistance. There was no failure observed from the small change in resistance during the bend test.

When bending the tube 180° to its bending limit, the outer radius was measured to be 1.50±0.06 mm, and the strain was 3.33±0.12% calculated with Equation 4. Even under this extreme bending condition, the 3.33% strain the wire experienced was smaller than the 4% ultimate strain of the standard straight bonding wires (p=0.091, 1-sample Wilcoxon Test). Therefore, with the smallest possible bending radius (inner radius), the wire helix is unlikely to break.

The results from the short-term tensile, torsion and bend tests support part of the third hypothesis that the device will survive short-term mechanical loading under surgical handling and extreme physiological conditions.

E. Fatigue Test

Figure 9:
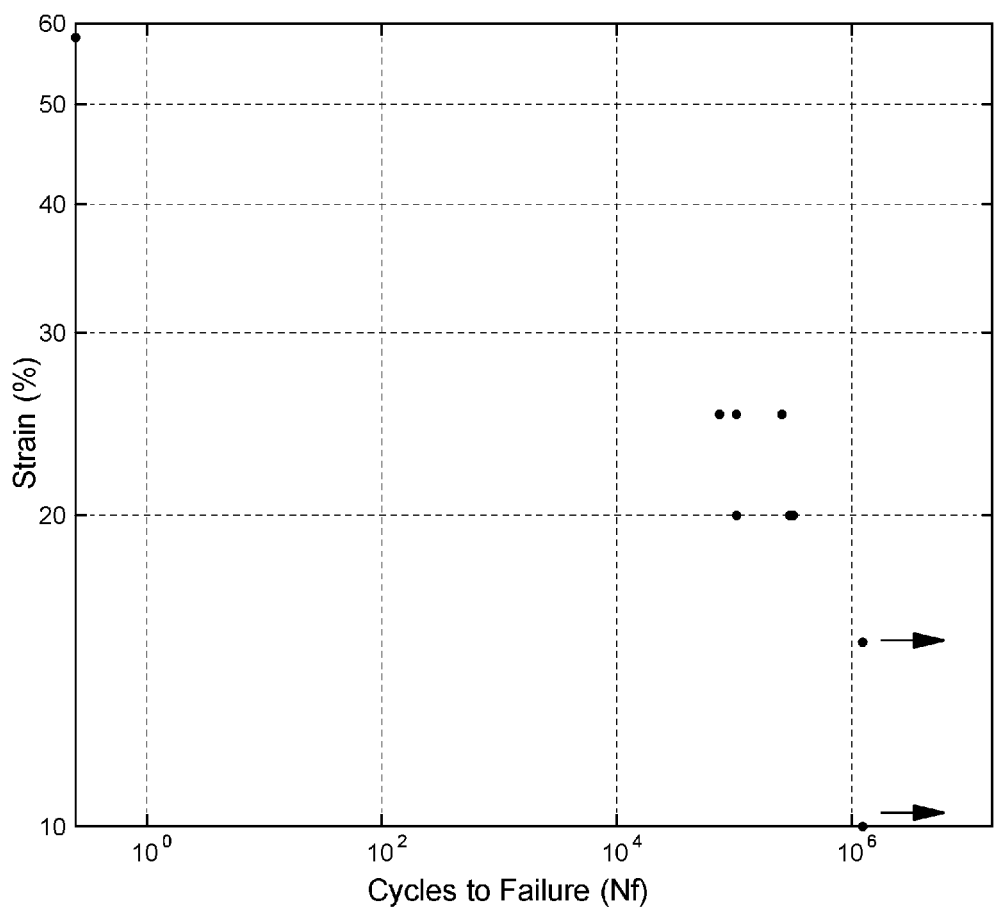
FIG. 9 is a graph showing the effect of repeated strain on cycles to failure for one example of the interconnect system (arrow indicates non-failure)

The effect of the change in percent of displacement (strain) on cycles to failure ($N_f$) is summarized in FIG. 9. As expected, the cycles to failure decrease when strain increases. This is due to the increased material deformation caused by larger strain. The three samples each tested with 15% and 10% strain separately did not lose electrical continuity after >1.2 million cycles. They were removed from the machine after it passed 1.2 million cycles.

Figure 10:
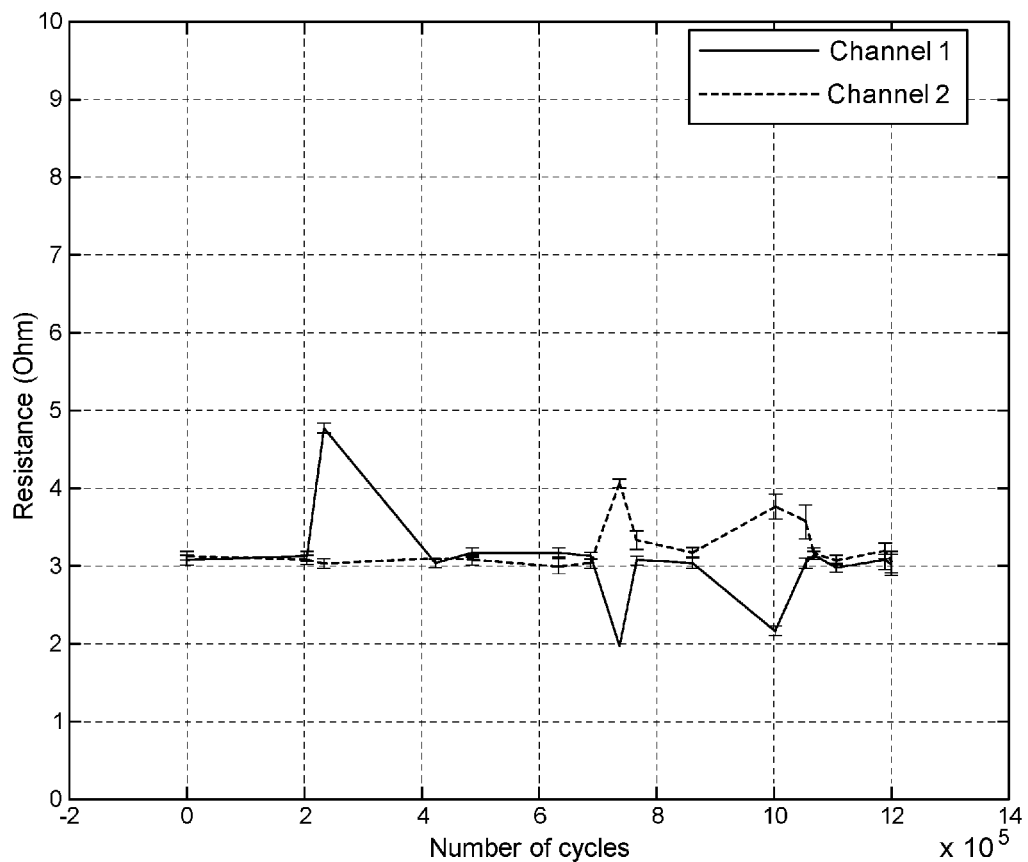
FIG. 10 is a graph showing resistance measurement from a fatigue test under 15% cyclic strain.

During each fatigue test, the resistance of each channel was recorded 2-4 times a day. FIG. 10 presents the resistance measurements of one sample tested 1.2 million cycles under 15% strain. The biggest change in the resistance goes from 3.1Ω to 4.7Ω. There was a maximum of 52% resistance change observed on this sample throughout the fatigue test.

Discussion

As shown in Equation 7, the determining factors on the device mechanical robustness are the tubing diameter and the separation between the helix and tubing due to their effect on the helix pitch angle.

$$\alpha = \tan^{-1} \frac{\pi(D + d + 2S)}{2nd} \qquad \text{Equation 7}$$

where α represents the helix pitch angle, D is the diameter of the tubing, S is the distance of the space between the microwire and tubing, n is the number of microwires, d is the diameter of the microwire, and 2nd represents the horizontal distance from the beginning of the previous wrap to the beginning of the following wrap assuming the pitch angle stays constant. The diameter of the tubing was selected to match the size of the previous interconnect system without being bulky on the z direction. The pitch angle is 61.55° assuming no empty space between the helix and tubing. When optimizing the design, it is desired to start with a large pitch angle by increasing the diameter of the tube and create space between helix and tube. From previous testing, a loosely wounded helix can stretch roughly 20% more compared to a tightly wounded helix. In addition, 35° was defined as the lower limit of the pitch angle as it fails at 16%-18% of axial displacement, thus suggesting 0.33 mm of tubing diameter with no space between the helix and the tube. The upper limit of the tubing diameter is constrained by the space at the implantation site.

A. Resistance Characteristics

The measured resistance across each bonding wire helix was found to be in the range of 0-10Ω. The estimated value 1.37Ω is about 2-3 times smaller compared to the experimental measurement. When measuring the resistance, the probes are attached to the free ends of the measuring wires. Any interface including the conductive epoxy that was used to connect measuring wires and bonding wires and the wire bonds on gold pads could increase the resistance. The resistance per unit length for the Ti/Pt thin film traces in flat configuration was measured to be 138.6 Ω/cm. Considering the traces have a much smaller cross sectional area (250 nm×50 μm) than the cross sectional area of bonding wires (25 µm²×(π/4)), the unit length resistance for bonding wire measured as 1.06 Ω/cm is significantly smaller compared to the unit length resistance for the thin film traces. The result supports the first hypothesis that the bonding wires reduce the channel resistance from the resistance of the thin film metal traces by 99.2%.

B. Response to Short-Term Stress or Strain

1. Ultimate Tensile Test

Figure 11:
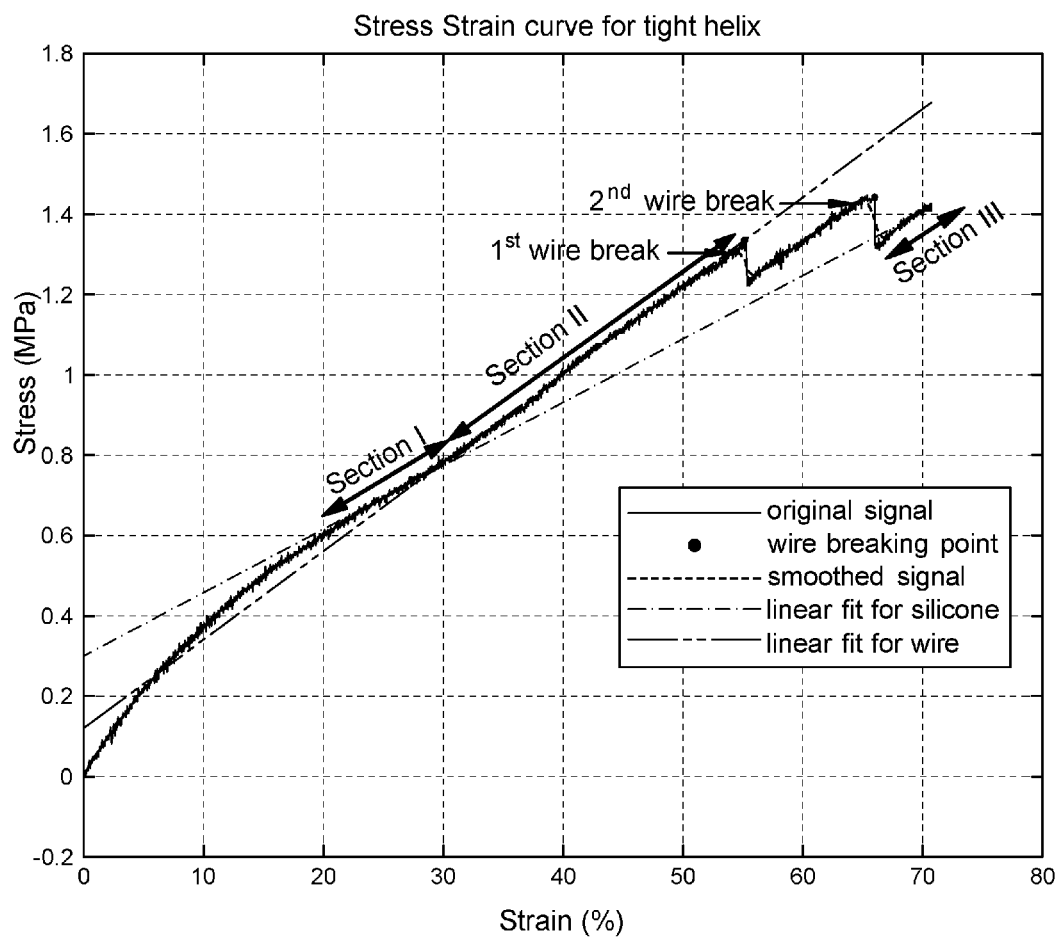
FIG. 11 is a stress-strain curve identical to FIG. 8 but indicating Sections I-III of the interconnect system.

The ultimate tensile failure point was recorded from the stress-strain curve shown as an example in FIG. 11. The force required for stretching the tube and the helices increased as the displacement increased. The stress-strain relationship in the elastic region is not entirely linear due to the force interaction between the helices and tube in the process of elongation. The sharp decrease at the first local maximum is due to the sudden drop in tension when one wire broke. The same process happened again when the system kept elongating and eventually caused the second wire to constrict on the tube.

As shown in FIG. 11, the stress strain curve has a changing slope before the first wire broke from section I to section II. Since the section III at the end of the curve represents the stress strain relationship of silicone tubing alone after both wires broke, the slope of section III is the estimated modulus for the silicone tubing along with the grips and load strain. The slope of section III matches with the slope of section I before the first wire broke, as indicated in the light blue fit line in FIG. 11. The average for the slope described above across the entire 10 samples is 1.51±0.23 MPa, which is assumed to be the modulus of the silicone tubing. Also, before the first wire broke, the slope of section II increased from the silicone tubing modulus as shown in the black trend line in FIG. 11. This second slope averaged across the 10 samples is 2.11±0.40 MPa. The second slope is higher than the first slope discussed above due to the fact that the silicone tubing was taking the majority of the load at first. Then after the helixes started to interact with the tube, the wire started to experience part of the load. The strain at the boundary between slope 1 and slope 2 is 37.11±16.60%. If the point of this slope change from section I to section II is the point when the microwire helix started to experience axial load, the strain should not be high enough to induce fatigue. However, the interconnect device started to break at 20% repeated axial strain during the fatigue tests, which is significantly smaller than the strain at the point of slope change ((p=0.004, 1-sample Wilcoxon Test).

By applying the blue line slope into Equation 7 assuming this slope represents the modulus of the supporting structure, the stress on the supporting structure and on the wire can be obtained.

$$\sigma_{tube} = E(\epsilon_2 - \epsilon_1) = 1.577 \times 10^6 \times (66.05\% - 55.4\%) = 0.168 \text{ MPa} \quad \text{Equation 8}$$

$$\sigma_{tube} = (\sigma_2 - \sigma_1) - \sigma_{tube} = (1.448 - 1.227) - 0.746 = 0.053 \text{ MPa} \quad \text{Equation 9}$$

The load on the tube and wire can be calculated by multiplying the distributed stress with each cross sectional area. The load on the tube was approximately 0.08 N, and the load on the wire was approximately $2.60 \times 10^{-5}$ N. The tube is serving as the stress relief mechanism to undertake majority of the load. In this way, the device will behave similar as the tubing with a larger ultimate strain (700%) compared to the ultimate strain of a 25 µm-diameter Au bonding wire (4%).

The measured ultimate tensile strain 58.21% is significantly larger than 4%, which is the standard ultimate failure strain for a 25 µm single bonding wire. This proves that bonding wires helix can elongate more than straight wires. It is also significantly larger than 18%, which is in reported as tensile failure point for peripheral nerves based on the past animal and cadaver studies. If the nerve is subjected to strains beyond 18%, it will lose microcirculation. Therefore, in one example, the device is not expected to be subjected to more strain than the nerve. The interconnect device tested will survive under the short-term maximum physiological condition if the device is implanted along the nerve.

2. Torsion Test

The torsion test showed different responses between rotating the helix clockwise versus counterclockwise based on the direction of the helix. The right-handed helices twisted with the tube until they broke when rotating one substrate counterclockwise relative to the other. In this condition, the system failed when one of the wires broke. One complete revolution is defined to be the most extreme condition to which the interconnect will be subjected to either in the body for a short time or during the surgical handling. The lower boundary of the confidence interval based on data in Table 3 is larger than 1 revolution. When the right-handed helices were rotated clockwise, the helices unwound from the tube. In this condition, the system failure is defined as when the helices started to separate from the tube. One sample was tested with clockwise rotation. The helices were partially separated from the tube after 3.57 revolutions. Then rotating the movable stage counterclockwise was not able to restore the original helical structure. The design validation tests have demonstrated that 5 samples passed the clockwise 180° and counterclockwise 180° torsion. The samples tested to ultimate failure point showed that the wire helices stayed connected past one complete cycle of rotation.

3. Bend Test

The bend test was performed to determine the mechanical and electrical response of the interconnect system under the extreme condition that may occur both when the device is implanted and during the surgical process. According to Table 4, the resistance value of each channel varied slightly, but the overall unit length resistance is still much smaller compared to the conductive thin film metal trace resistance. Since it was observed that the resistance would become infinite when the wire was no longer continuous, any change that is within 100% of the original resistance is not considered involving any major mechanical deformation. The upper boundary of the five bending radii was selected based on the length of the helical structure while the rest were selected randomly. Although the bend test did not investigate bending radii smaller than the selected range, the prediction based on the extreme bending condition indicates that the wires are unlikely to break even when the tube was flattened out at the bending point.

C. Response to Cyclical Strain

The fatigue-life behavior in FIG. 9 was analyzed using the Coffin-Manson-Basquin relationship. The Coffin-Manson-Basquin relationship has shown close fit to the experimental results on multi-strand metal cable. The fatigue strength exponent and fatigue ductility exponent are calculated by fitting the data with the Coffin-Manson-Basquin equation and found to be in the exponent ranges for the structural metals. However, the helix and silicone tube interconnect system does not fall in the category of structural metals. Finding the Coffin-Manson-Basquin fit curve based on experimental data would not present meaningful strength exponent and ductility exponent since these values are based solely on single component samples and the current test has been performed on a silicone tube plus wire system.

Equation 9, the Universal slope equation was proposed as an alternative form of Coffin-Manson-Basquin relationship from correlating the strain and fatigue-life relationship of 29 different materials.

$$\Delta \varepsilon = \left(\frac{3.5S_u}{E}\right)(N_f)^{-0.12} + D^{0.6}(N_f)^{-0.6} \qquad \text{Equation 10}$$

$$D = \ln\left(\frac{100}{100 - \% \, RA}\right) \qquad \text{Equation 11}$$

where $\Delta \varepsilon$ is the strain amplitude, $S_u$ the ultimate tensile strength, E the elastic modulus, $N_f$ the cycles to failure, D the ductility, and % RA is the percent of reduction in area. The minimum diameter of the neck on the broken wire was estimated to be 5 µm. The percent of reduction in area can be calculated with Equation 11.

$$\% \, RA = \frac{\pi 25^2 - \pi 5^2}{\pi 25^2} = 96\% \qquad \text{Equation 12}$$

The modified universal slopes equation below was proposed based on fatigue test data from 50 different materials.

$$\Delta \varepsilon = \qquad \text{Equation 12}$$
$$1.17\left(\frac{S_u}{E}\right)^{0.832}(N_f)^{-0.09} + 0.0266 D^{0.155}\left(\frac{S_u}{E}\right)^{-0.53}(N_f)^{-0.56}$$

The uniaxial tensile data reported in Table 5 was used to predict the fatigue response of straight Au bonding wire.

TABLE 5

Property of straight 25 µm diameter Au bonding wire at 27° C.

| Electrical Resistivity (Ω-cm) | Elastic modulus (GPa) | Yield strength (MPa) | Ultimate tensile strength (MPa) | Poisson's ratio | Elongation (%) |
|---|---|---|---|---|---|
| $2.2 \times 10^{-6}$ | 77.2 | 172.38 | 206.85 | 0.291 | 4 |

*There is no standard property for helical wires

Figure 12:
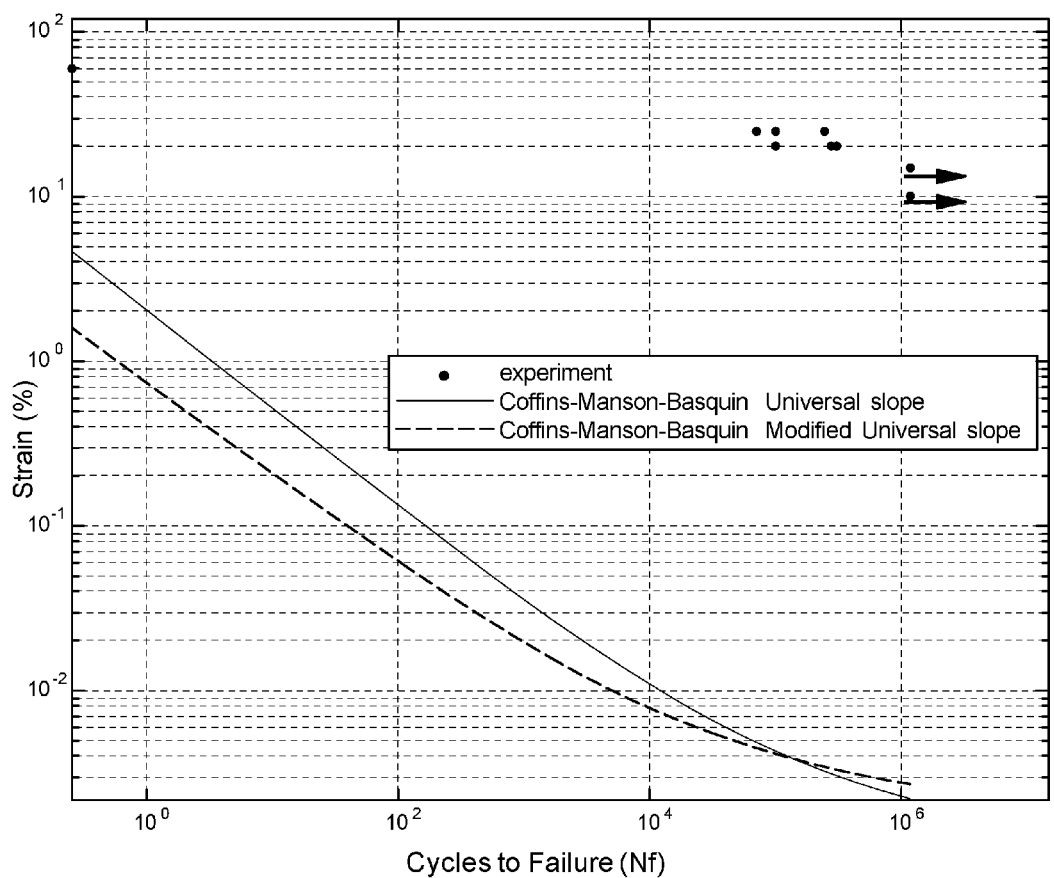
FIG. 12 is a graph showing fatigue response and predicted strain-life behavior of Au straight bonding wire using ultimate strength and modulus from Table 5.

The predicted Coffin-Manson-Basquin relationship for a straight 25 µm-diameter Au bonding wire using both universal slopes and modified universal slope are shown in FIG. 12 to compare with the experimental fatigue data of the interconnect system including the microwire helices and silicone tube.

FIG. 12 indicates that under strains lower than the tested strains, the straight Au bonding wire is predicted to fail at much lower cycles. According to the calculated relationship, the straight bonding wires will not be able to pass 1 cycle under the strain tested on the interconnect device. This comparison with the tensile test data supports the concept that the interconnect system has demonstrated an improved ability to elongate compared to the straight bonding wires through both large short-term mechanical deformations during the surgical procedure, and smaller long-term mechanical deformations while implanted.

To predict for the interconnect strain-life relationship, the ultimate tensile strength and modulus of the interconnect device were used in conjunction with Equations 9 and 11.

Figure 13:
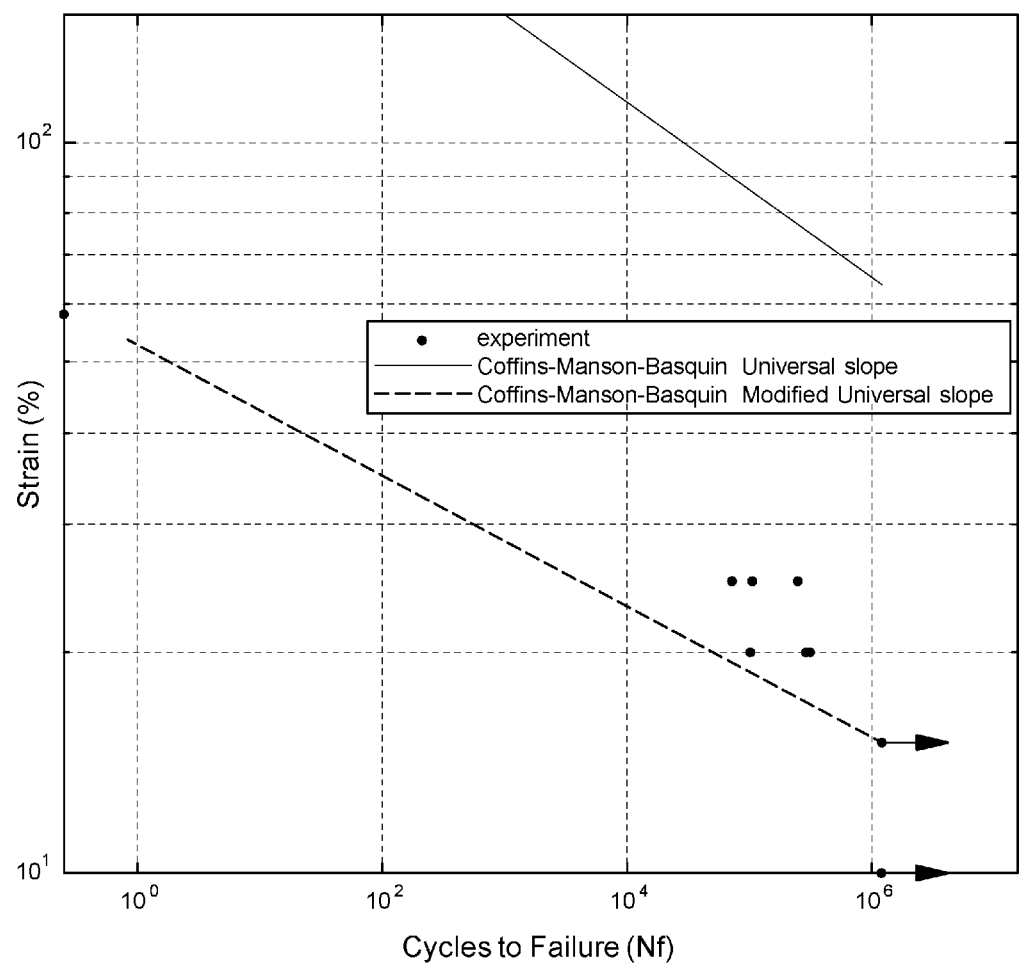
FIG. 13 is a graph showing predicted strain-life behavior of the interconnect system using experimentally-measured modulus from tensile test and standard Au bonding wire.

The ultimate tensile strength of the interconnect system is 206.85 MPa (Table 5), which should be the same as the tensile strength of the standard 25 µm Au bonding wire assuming no additional stress from the edge of the bond chips. The modulus of the system is estimated by the slope of the section of the stress strain curves before system failure, which is 2.11 MPa (see above). This modulus is not the same as the modulus of the straight Au bonding wire provided in Table 5. FIG. 13 reveals that the modified slope is relatively close to the experimental data, while the universal slopes equation significantly over-predicted the fatigue life.

During the test, the resistance of each channel was measured periodically. The unit length resistance across the bonding wires was in the range of 0.71 to 1.56 Ω/cm, which is much smaller compared to the thin film traces unit length resistance 138.6 Ω/cm. The resistance value of each channel changed throughout the testing period, but all the changes are relatively small compared to the resistance of the conductive thin film traces. Therefore, the resistance changes shown in FIG. 10 were not considered significant enough to indicate any major structural deformation on the wires.

From the above description, those skilled in the art will perceive improvements, changes and modifications. Such improvements, changes, and modifications are within the skill of one in the art and are intended to be covered by the appended claims.

The following is claimed:

1. An interconnect device comprising:
   a flexible bridge having a length and an outer surface and comprising a main body portion extending between oppositely disposed first and second ends, each of the first and second ends configured for connection to an electrical contact; and
   a non-linear conductive transmission line extending along, and encircling at least a portion of, the length of the bridge;
   wherein, upon the connection, the main body portion is configured to be freely suspended between the electrical contacts.

2. The device of claim 1, wherein the flexible bridge is hollow.

3. The device of claim 1, wherein the flexible bridge has a tubular configuration.

4. The device of claim 1, wherein the flexible bridge is made of silicone.

5. The device of claim 1, wherein the non-linear conductive transmission line is a microwire.

6. The device of claim 5, wherein the microwire is made of at least one of aluminum, copper or gold.

7. The device of claim 5, wherein the microwire has a diameter of between about 20 µm to about 75 µm.

8. The device of claim 1, wherein the non-linear conductive transmission line has a helical shape.

9. The device of claim 8, wherein at least a portion of the non-linear conductive transmission line is in direct contact with the outer surface of the flexible bridge.

10. The device of claim 8, wherein the non-linear conductive transmission line is radially spaced apart from, and free from direct contact with, the outer surface of the flexible bridge.

11. An interconnect system for bridging electrical contacts, the system comprising:
   a first electrical contact;
   a second electrical contact; and an interconnect device coupled to and extending between the first and second electrical contacts, the interconnect device comprising:
- a flexible bridge having a length and an outer surface and comprising a main body portion extending between oppositely disposed first and second ends, each of the first and second ends coupled to a respective electrical contact, wherein the main body portion is freely suspended between the first electrical contact and the second electrical contact; and
- a non-linear conductive transmission line extending along, and encircling at least a portion of, the length of the bridge such that the non-linear conductive transmission line electrically connects the first electrical contact with the second electrical contact.

12. The system of claim 11, being sufficiently flexible such that upon bending or deformation, the interconnect device bends or deforms with the rest of the system so that the electrical connection between the first and second electrical contacts is not broken.

13. The system of claim 11, wherein the flexible bridge is made of silicone.

14. The system of claim 11, wherein the non-linear conductive transmission line is a helical microwire.

15. The system of claim 11, wherein at least a portion of the non-linear conductive transmission line is in direct contact with the outer surface of the flexible bridge.

16. The device of claim 11, wherein the non-linear conductive transmission line is radially spaced apart from, and free from direct contact with, the outer surface of the flexible bridge.

17. An implantable neurostimulator comprising:
a first electrical contact;
a second electrical contact; and
an interconnect device coupled to and extending between the first and second electrical contacts, the interconnect device comprising:
- a flexible bridge having a length and an outer surface and comprising a main body portion extending between oppositely disposed first and second ends, each of the first and second ends coupled to a respective electrical contact, wherein the main body portion is freely suspended between the first electrical contact and the second electrical contact; and
- a non-linear conductive transmission line extending along, and encircling at least a portion of, the length of the bridge such that the non-linear conductive transmission line electrically connects the first electrical contact with the second electrical contact.

18. The neurostimulator of claim 17, wherein the first and second electrical contacts comprise a high-density array.

19. The neurostimulator of claim 17, being sufficiently flexible such that upon bending or deformation, the interconnect device bends or deforms with the rest of the system so that the electrical connection between the first and second electrical contacts is not broken.

20. The neurostimulator of claim 17, wherein the non-linear conductive transmission line is a helical microwire that is radially spaced apart from, and free from direct contact with, the outer surface of the flexible bridge.

* * * * *